United States Patent [19]

Tokuyama

[11] Patent Number: 5,916,774

[45] Date of Patent: Jun. 29, 1999

[54] D-AMINOACYLASE

[75] Inventor: Shinji Tokuyama, Shizuoka, Japan

[73] Assignee: Daicel Chemical Industries, Ltd., Osaka, Japan

[21] Appl. No.: 09/122,386

[22] Filed: Jul. 24, 1998

[30] Foreign Application Priority Data

Jul. 31, 1997 [JP] Japan ................................ 9-206288
May 22, 1998 [JP] Japan ................................ 10-141932

[51] Int. Cl.$^6$ .............................. C12P 21/04; C07K 1/00; C07K 14/00; C07K 17/00
[52] U.S. Cl. .......................................... 435/71.2; 530/350
[58] Field of Search .......................... 530/350; 435/71.1, 435/71.2

[56] References Cited

PUBLICATIONS

Kameda et al., "Studies on Acylase Activity and Micro–organisms", Chem. Pharm. Bult., 26(9):2698–2704, 1978.

Moriguchi et al., "Production, Purification, and Characterization of D–Aminoacylase from *Alicaligenes xylosoxydans* subsp. *xylosoxydans* A–6", Siosc. Biotech. Biochem., 57:1149–1152, 1993.

Sakai et al., "Purification and Properties of D–Aminoacylase from *Alcaligenes denitrificans* subsp. *xylosoxydans* MI–4", J. of Fermentation and Bioeng., 71:79–82, 1991.

Sugie et al., "Purification and Properties of D–Aminoalcylase of *Streptomyces olivaceus*", Agric. Biol. Chem., 42:107–113, 1978.

Sugie et al., "Optical Resolution of DL–Amino Acids with D–Aminoacylase of Streptomyces", Agric. Biol. Chem., 44:1089–1095, 1980.

*Primary Examiner*—Robert A. Wax
*Assistant Examiner*—Devesh Srivastava
*Attorney, Agent, or Firm*—Fish & Richardson P.C.

[57] ABSTRACT

This invention provides a novel D-aminoacylase and a method for producing said enzyme, and also a method for producing D-amino acids using said aminoacylase. D-aminoacylase of the invention having novel properties can be derived from a microorganisms belonging to genus Amycolatopsis. The use of the enzyme enables industrial production of D-amino acids.

8 Claims, 8 Drawing Sheets

D-AMINOACYLASE

FIELD OF THE INVENTION

The present invention relates to a novel D-aminoacylase, a method for producing the same, and a method for producing D-amino acid using said aminoacylase.

BACKGROUND OF THE INVENTION

Enzymes have not only high catalytic activity but also stereospecificity for catalysis as well as substrate specificity and reaction specificity. The enzyme stereospecificity is almost absolutely strict with a few exceptions.

With the recent development of precision research, usage of optical isomers has become increasingly important in the field of medicines, agricultural chemicals, feeds, perfumes, etc. This is because optical isomers are often completely different in their biological activities. For example, in the case of thalidomide, its D(R)-isomer is not teratogenic, but the L(S)-isomer is strongly teratogenic. The practical use of its racemate as medicine caused the drug hazard scandal. Furthermore, when one of the antipodes shows effective biological activity and another not only shows no activity at all but also acts as a competitive inhibitor to the effective antipode, the raceme's biological activity is often reduced to one half of that of the effective antipode or lower. Therefore, the availability of optically pure antipode (by synthesis or resolution) has become an industrially important issue. For this purpose, such techniques have been widely used as to synthesize racemate and to optically resolve it effectively and much attention has been paid on the optical resolution with enzyme, which does not generate side products and a large amount of waste solution.

In general, L-amino acids are used widely and in large quantities as seasonings, food/feed additives, medical transfusion solution, etc. and, thus, their utilization value is extremely high. While L-amino acids are produced mainly by the direct fermentation method using microorganisms, there has been also known the optical resolution method to produce L-amino acids by (stereospecifically) hydrolyzing N-acyl-DL-amino acids with L-aminoacylase. This method has been used conventionally for the industrial production of L-amino acids that are hardly producible by the fermentation method. The L-aminoacylase used in this method is widely distributed in animals, plants, and microorganisms. The enzymes derived from various biological sources have been purified and elucidated of their enzymological properties. Also, since the N-terminal amino acid of many proteins are thought to be acetylated in vivo, L-aminoacylase is considered to function in regenerating amino acid from N-acetyl-amino acid produced by degradation of proteins. In addition, of these L-aminoacylases, the one acting on N-acyl-L-glutamic acid has been thought to participate in the biosynthesis of arginine (Fruh, H., Leisinger, T., J. Gen. 125, pp1 (1981)).

On the other hand, since D-amino acids are non-proteinaceous amino acids, they have not been of practical interest for a long time. In nature, existence of D-amino acids is limited to small cyclic peptides, peptidoglycans of bacterial cell wall, and peptide antibiotics. However, it has been elucidated that D-amino acids are present in the bound form in the constitutive component of neuropeptides, tooth enamelum, eye lens, and cerebral proteins, and the elucidation of physiological significance of D-amino acids and the research on enzymatic methods for producing them have been actively pursued.

At present, resolution of DL-amino acids is carried out by physicochemical, chemical, and enzymatic methods. Among them, the enzymatic method is most convenient, and a method for continuously producing L-methionine from N-acetyl-DL-methionine using a bioreactor with immobilized L-aminoacylase has been industrialized. One of the methods for producing D-amino acids utilizes hydantoinase. This method comprises two enzymatic steps of D-carbamyl derivative formation by the action of D-specific hydantoinase on DL-5-substituted hydantoin as the starting material, which can be synthesized from aldehyde analog economically, and the subsequent action of D-amino acid carbamilase. Another known method for producing D-amino acids comprises hydrolyzing N-acetyl-DL-amino acids using D-aminoacylase [Sugie, M. and Suzuki, H., Agric. Biol. Chem. 44, pp1089 (1980), Tsai, Y. C., Lin, C. S., Tseng, T. H., Lee H., and Wang, Y., J. Enzyme Microb. Technol. 14, pp384 (1992)]. In spite of the importance of D-aminoacylase for the production of D-amino acids, its physiological significance and structural function have not been elucidated yet.

The first report of the presence of D-aminoacylase was made by Kameda et al. in 1952 in Pseudomonas sp. KT83 isolated from soil [Kameda, Y., Toyoura, H., Kimura, Y., and Yasuda, Y., Nature 170, pp888 (1952)]. This enzyme hydrolyzed N-benzoyl derivatives of D-phenylalanine, D-tyrosine, and D-alanine. Since then, D-aminoacylases derived from the following sources have been reported: genus Pseudomonas [Kubo, K., Ishikura, T. and Fukagawa, Y., J. Antibiot. 43, pp550 (1980), Kubo, K., Ishikura, T. and Fukagawa, Y., J. Antibiot. 43, pp556 (1980), Kameda, Y., Hase, T., Kanatomo, S., and Kita, Y., Chem. Pharm. Bull. 26, pp2698 (1978), Kubo, K., Ishikura, T., and Fukagawa, Y., J. Antibiot. 43, pp543 (1980)], genus Streptomyces [Sugie, M. and Suzuki, H., Agric. Biol. Chem. 42, pp107 (1978), Sugie, M. and Suzuki, H., Agric. Biol. Chem. 44, pp1089 (1980), genus Alcaligenes (Tsai, Y. C., Tseng, C. P., Hsiao, K. M., and Chen, L. Y., Appl. Environ. Microbiol. 54, pp984 (1988), Yang, Y. B., Hsiao, K. M., Li, H., Yano, Y., Tsugita, A., and Tsai, Y. C., Biosci. Biotech. Biochem. 56, pp1392 (1992), Yang, Y. B., Lin, C. S., Tseng, C. P., Wang, Y. J., and Tsai, Y. C., Appl. Environ. Microbiol. 57, pp2767 (1991), Tsai, Y. C., Lin, C. S., Tseng, T. H., Lee, H., and Wang, Y. J., Microb. Technol. 14, pp384 (1992), Moriguchi, M. and Ideta, K., Appl. Environ. Microbiol. 54, pp2767 (1988), Sakai, K., Imamura, K., Sonoda, Y., Kido, H., and Moriguchi, M., FEBS, 289, pp44 (1991), Sakai, K., Obata, T., Ideta, K., and Moriguchi, M., J. Ferment. Bioeng. 71, pp79 (1991), Sakai, K., Oshima, K., and Moriguchi, M., Appl. Environ. Microbiol. 57, pp2540 (1991), Moriguchi, M., Sakai, K., Katsuno, Y., Maki, T., and Wakayama, M., Biosci. Biotech. Biochem. 57, pp1145 (1993), Wakayama, M., Ashika, T., Miyamoto, Y., Yoshikawa, T., Sonoda, Y., Sakai, K., and Moriguchi, M., J. Biochem. 118, pp204 (1995), Moriguchi, M., Sakai, K., Miyamoto, Y., and Wakayama, M., Biosci. Biotech. Biochem. 57, pp1149 (1993)].

In addition, Tsai et al. and Moriguchi et al. characterized D-aminoacylase derived from bacteria belonging to genera Alcaligenes and Pseudomonas, and further elucidating the amino acid sequence of the enzyme protein and the base sequence of the gene thereof. Moriguchi et al. found that bacteria belonging to genera Alcaligenes and Pseudomonas produced three different kinds of D-aminoacylase in response to the change of inducers [Wakayama, M., Katsuno, Y., Hayashi, S., Miyamaoto, Y., Sakai, K., and Moriguchi, M., Biosci. Biotech. Biochem. 59, pp2115 (1995)].

Furthermore, Moriguchi et al. determined DNA sequences of genes coding for these D-aminoacylases derived from genus Alcaligenes, and compared them with those of L-aminoacylases derived from *Bacillus stereothermophilus*, humans and swine, reporting, as a result, a low homology in the gene structure between these D-aminoacylases and L-aminoacylases [Wakayama, M., Katsuno, Y., Hayashi, S., Miyamoto, Y., Sakai, K., and Moriguchi, M., Biosci. Biotech. Biochem. 59, pp2115 (1995)].

On the other hand, as to Actinomycetes, Sugie et al. reported the presence of D-aminoacylase in genus Streptomyces, but did not purify the enzyme to fully elucidate its properties [Sugie, M. and Suzuki, H., Agric. Biol. Chem. 42, pp107 (1978), Sugie, M. and Suzuki, H., Agric. Biol. Chem. 44, pp1089 (1989)].

SUMMARY OF THE INVENTION

An object of the present invention is to provide a novel D-aminoacylase and a method for producing the same. Another object of the present invention is to provide a method for producing D-amino acids utilizing said D-aminoacylase.

The present inventors have intensively studied to solve the above-described problems, and, as a result, succeeded in purifying a D-aminoacylase with novel properties from a microorganism belonging to the genus Amycolatopsis by a combination of various purification techniques. Furthermore, the present inventors found that the purified D-aminoacylase is useful for the industrial production of D-amino acids.

That is, the present invention relates to a novel D-aminoacylase and a method for producing said enzyme as well as a method for producing D-amino acids using said D-aminoacylase, more specifically relates to (1) D-aminoacylase having the following physicochemical properties,
  (a) action: it acts on N-acetyl-D-amino acids to produce corresponding D-amino acids;
  (b) molecular weight: it has the molecular weight of about 36,000 dalton when measured by SDS-polyacrylamide gel electrophoresis;
  (c) substrate specificity: it acts on N-acetyl-D-methionine, N-acetyl-D-valine, N-acetyl-D-tryptophan, N-acetyl-D-asparagine, N-acetyl-D-phenylalanine, N-acetyl-D-alanine, and N-acetyl-D-leucine, but not on N-acetyl-L-methionine, N-acetyl-L-leucine, and N-acetyl-L-valine;
  (d) thermostability: when heated at pH 7.5 for 30 min, it is relatively stable at 40° C., but inactivated at not less than 50° C.;
  (e) optimal temperature: when reacted at pH 7.5, it optimally acts at about 35° C.;
  (f) optimal pH: when reacted at 30° C. for 60 min, it optimally acts at about pH 8.0; and
  (g) influences of metallic ions: its enzyme activity is promoted by 1 mM $Co^{2+}$ or $Ca^{2+}$, but inhibited by 1 mM $Cu^{2+}$, $Hg^{2+}$, or $Zn^{2+}$, (2) the D-Aminoacylase according to (1) above derived from a microorganism belonging to genus Amycolatopsis, (3) a method for producing D-aminoacylase, which comprises culturing a microorganism belonging to genus Amycolatopsis and recovering from the cultured microbial cells an enzyme having the following physicochemical properties:
  (a) action: it acts on N-acetyl-D-amino acids to produce corresponding D-amino acids;
  (b) molecular weight: it has the molecular weight of about 36,000 dalton when measured by SDS-polyacrylamide gel electrophoresis;
  (c) substrate specificity: it acts on N-acetyl-D-methionine, N-acetyl-D-valine, N-acetyl-D-tryptophan, N-acetyl-D-asparagine, N-acetyl-D-phenylalanine, N-acetyl-D-alanine, and N-acetyl-D-leucine, but not on N-acetyl-L-methionine, N-acetyl-L-leucine, and N-acetyl-L-valine;
  (d) thermostability: when heated at pH 7.5 for 30 min, it is relatively stable at 40° C., but inactivated at not less than 50° C.;
  (e) optimal temperature: when reacted at pH 7.5, it optimally acts at about 35° C.;
  (f) optimal pH: when reacted at 30° C. for 60 min, it optimally acts at about pH 8.0; and
  (g) influences of metallic ions: its enzyme activity is promoted by 1 mM $Co^{2+}$ or $Ca^{2+}$, but inhibited by 1 mM $Cu^{2+}$, $Hg^{2+}$, or $Zn^{2+}$.

(4) a method for producing D-amino acids, which comprises reacting said D-aminoacylase described in (1) above with N-acetyl-DL-amino acids, and (5) the method according to (4), wherein said N-acetyl-DL-amino acid is selected from the group consisting of N-acetyl-DL-methionine, N-acetyl-DL-valine, N-acetyl-DL-tryptophan, N-acetyl-DL-asparagine, N-acetyl-DL-phenylalanine, N-acetyl-DL-alanine, and N-acetyl-DL-leucine.

DETAILED DESCRIPTION OF THE INVENTION

Figure 1:
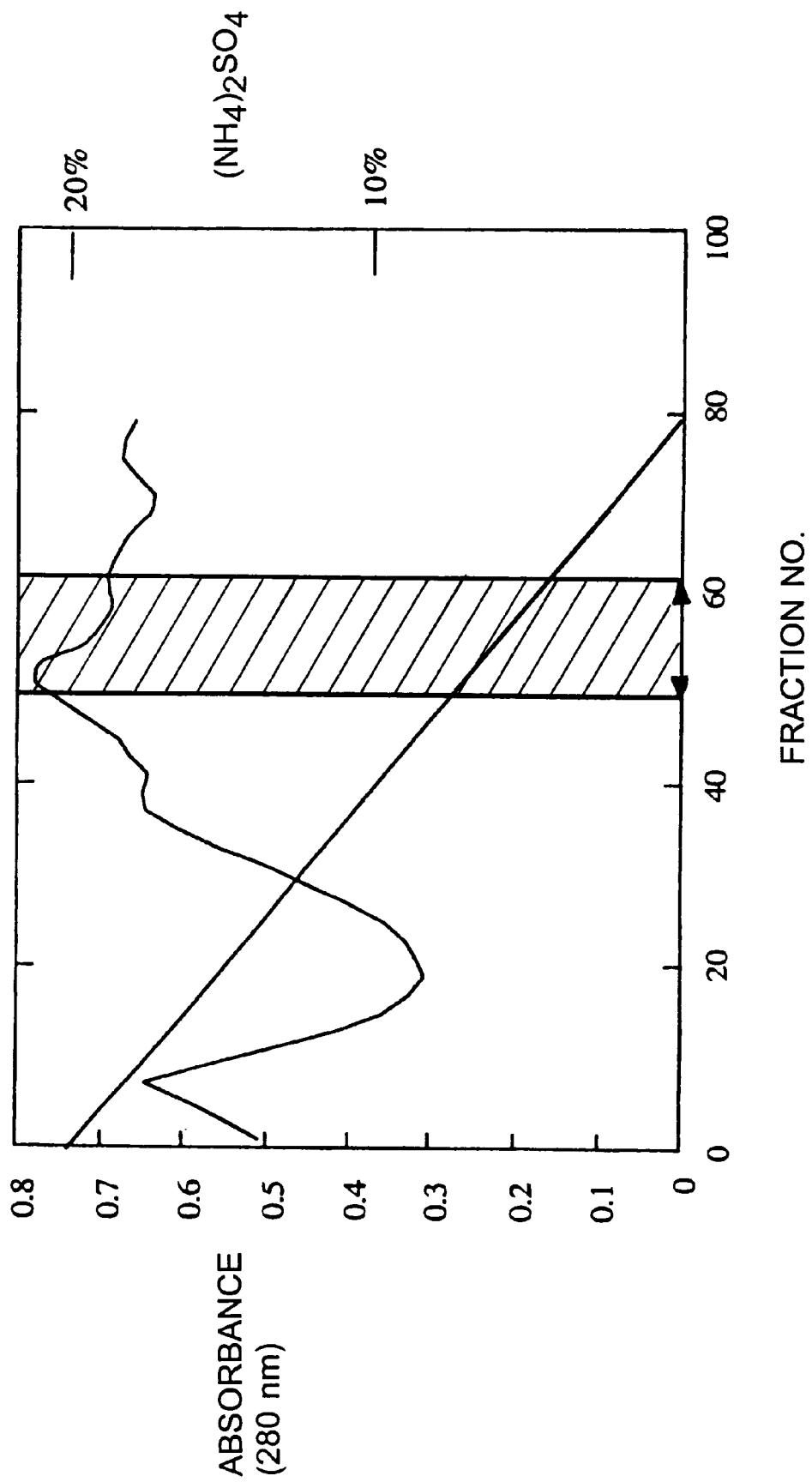
FIG. 1 shows the purification of D-aminoacylase of the present invention by Butyl-Toyopearl column chromatography. Arrows indicate active fractions. (fractions No. 50 to No. 62).

The present invention relates to a novel D-aminoacylase. The D-aminoacylase of the present invention has the following physicochemical properties: (a) action: it acts on N-acetyl-D-amino acids to produce corresponding D-amino acids; (b) molecular weight: it has the molecular weight of about 36,000 dalton when measured by SDS-polyacrylamide gel electrophoresis; (c) substrate specificity: it acts on N-acetyl-D-methionine, N-acetyl-D-valine, N-acetyl-D-tryptophan, N-acetyl-D-asparagine, N-acetyl-D-phenylalanine, N-acetyl-D-alanine, and N-acetyl-D-leucine, but not on N-acetyl-L-methionine, N-acetyl-L-leucine, and N-acetyl-L-valine; (d) thermostability: when heated at pH 7.5 for 30 min, it is relatively stable at 40° C., but inactivated at not less than 50° C.; (e) optimal temperature: when reacted at pH 7.5, it optimally acts at about 35° C.; (f) optimal pH: when reacted at 30° C. for 60 min, it optimally acts at about pH 8.0; and (g) influences of metallic ions: its enzyme activity is promoted by 1 mM $Co^{2+}$ or $Ca^{2+}$, but inhibited by 1 mM $Cu^{2+}$, $Hg^{2+}$, or $Zn^{2+}$.

There is no particular limitation as to the origin of D-aminoacylase of the present invention so far as it has properties as described above. The enzyme is exemplified by D-aminoacylase derived from microorganisms belonging to genus Amycolatopsis, specifically *Amycolatopsis orientalis*, more specifically *Amycolatopsis orientalis* IFO 12806 (as listed in List of Cultures, Institute for Fermentation, Osaka (1996) and available from the Institute). The microorganism to be used may be wild strains, variants, or recombinant strains produced by genetic techniques such as cell fusion or gene manipulation.

The D-aminoacylase of the present invention can be prepared using the method for assaying the enzymatic activity and purifying said enzyme as described in the following Examples. Specifically, the enzyme can be prepared by culturing the above-described microorganism under the conditions that it produces the desired enzyme and recovering the enzyme having the above-described physicochemical properties from the cultured microbial cells.

The culture medium used for culturing the microorganism to be used in the present invention is not particularly limited as long as the microorganism can proliferate therein. Any carbon source, which is usable by the above-described microorganism, can be used. Examples thereof include sugars such as glucose, fructose, sucrose, and dextrin, alcohol such as sorbitol and glycerol, organic acids such as fumaric acid, citric acid, acetic acid, and propionic acid and the salts thereof, hydrocarbons such as paraffin, and mixtures of these materials. Examples of nitrogen sources include ammonium salts of inorganic acids such as ammonium chloride, ammonium sulfate, and ammonium phosphate, ammonium salts of organic acids such as ammonium fumarate, and ammonium citrate, meat extract, yeast extract, corn steep liquor, hydrolysate of casein, inorganic or organic nitrogen-containing compounds such as urea, and mixtures of these materials. In addition, nutrients that are used for ordinary culture such as organic salts, trace mineral salts, and vitamins may be mixed as needed.

The microorganism is cultured in the presence of an inducer for the enzyme production. Examples of the inducer include N-acetyl-DL-methionine, DL-valine, or the like.

The microorganism can be cultured under any condition that it grows. Specifically, culturing can be carried out in the culture medium at the pH of usually 2 to 12, preferably 4 to 10, and at the temperature of usually 5 to 60° C., preferably 20 to 40° C., for the culturing period of usually several hours to ten days until activity of the enzyme produced becomes maximum.

The enzyme produced can be recovered by collecting the cultured microbial cells from the culture medium by, for example, centrifugation, disrupting the cells by, for example, ultrasonication, lysis with lysozyme, or the like. The thus-obtained cell-free extract is subjected to various purification methods usually used in the art, including ion exchange chromatography, gel filtration, fractionation with ammonium sulfate, and the like to give the purified enzyme.

Since D-aminoacylase of the present invention has the property to act on various N-acetyl-D-amino acids to yield D-amino acids as described above, it is useful for the industrial production of D-amino acids. For example, D-amino acid can be produced by reacting D-aminoacylase of the present invention with N-acetyl-DL-amino acids. Usable N-acetyl-DL-amino acids include N-acetyl-DL-methionine, N-acetyl-DL-valine, N-acetyl-DL-tryptophan, N-acetyl-DL-asparagine, N-acetyl-DL-phenylalanine, N-acetyl-DL-alanine, and N-acetyl-DL-leucine.

In the production of D-amino acids according to the present invention, it is possible to use not only the purified enzyme but also the crude enzyme as obtained above, the cultured microorganism, and the treated products of the microorganism. The microorganism can be used in a state of the culture medium, cells separated from the culture medium by centrifugation or the like, or cells resuspended in buffer, water, or the like after they are separated by centrifugation and washed. The microbial cells can be used in a state as they are recovered, as their disrupts, as treated with acetone or toluene, or as lyophilizate. The microbial cells can also be used after immobilization with carageenan gel, alginate gel, polyacrylamide gel, cellulose, or agar using a known method.

There is no particular limitation of the concentration of N-acetyl-DL-amino acids, which is the substrate, but the concentration of about 0.1 to 30% is usually used. The reaction is often accelerated with the use of a large amount of D-aminoacylase, but the enzyme is usually employed at the concentration of about 1 U to 1000 U/ml, where one unit of enzyme is defined as the amount of enzyme to produce 1 μmol of D-methionine at 30° C. in 1 min when the enzyme is reacted with N-acetyl-DL-methionine as the substrate. The reaction is performed at 5 to 50° C., preferably 30 to 40° C., and pH 4 to 10, preferably 7 to 9. The enzyme is often stabilized by immobilizing it on polyacrylamide, etc. The reaction time depends on the amount of both D-aminoacylase and substrate, and usually the reaction is often completed in 10 to 100 h, preferably 10 to 50 h. The reaction medium to be used includes water, a buffer, an aqueous organic solvent such as alcohols, and a double phase solution of water and a water-immiscible organic solvent such as toluene.

D-Amino acid formed by the reaction from the reaction solution can be recovered by known methods such as the direct crystallization through concentration, isoelectric precipitation, etc., treatment with ion exchange resin, membrane filtration, etc. For example, in the case of preparing D-tryptophan from the substrate N-acetyl-DL-tryptophan, D-tryptophan may be isolated from the reaction solution by passing the reaction solution through a strongly acidic cation exchange resin to absorb D-tryptophan, washing the resin with water, and eluting the amino acid with 0.5 N ammonia water. After concentrating the resulting effluent to give crystalline powder of crude D-tryptophan, it is dissolved in a small amount of 50% hot ethanol, decolonized by treatment with active charcoal and cooled to recover purified crystalline D-tryptophan. In the case of D-valine, after the completion of reaction, the reaction solution is centrifuged to remove microorganisms, brought to pH 1 with 6 N HCl, and centrifuged to remove N-Acetyl-L-valine precipitated. The supernatant is treated with active charcoal, brought again to pH 7.0, applied to strongly acidic H⁺-type cation exchanger (Amberite IR-120B), and eluted with 5% ammonia water. D-valine can be obtained by evaporating the effluent to dryness under reduced pressure at 80° C.

The present invention provides a novel D-aminoacylase derived from a microorganism belonging to genus Amycolatopsis as well as a method for producing said enzyme, and also a method for producing D-amino acids using said D-aminoacylase. The use of D-aminoacylase of the present invention enables the convenient and efficient production of corresponding D-amino acids from N-acetyl-DL-amino acids (e.g. N-acetyl-DL-methionine, N-acetyl-DL-valine, N-acetyl-DL-tryptophan, N-acetyl-DL-asparagin, N-acetyl-DL-phenylalanine, N-acetyl-DL-alanine, N-acetyl-DL-leucine, etc.).

In the following, the present invention will be described with reference to Examples, which are not intended to limit the scope of the invention.

EXAMPLE 1

(1) Microbial Strain and Culture

A 100-ml portion each of ISP-2 liquid medium containing 0.4% yeast extract (Oriental Yeast), 1.0% malt extract (Difco), and 0.4% glucose (Sanei Toka), at pH 7.3, supplemented with 0.1% N-acetyl-DL-methionine (Sigma) as an inducer, was placed in 500-ml Erlenmeyer flasks, sterilized with a speed autoclave, and used as the culture medium for *Amycolatopsis orientaris* IFO 12806 to produce D-aminoacylase. Flasks were incubated on a rotatory shaker at 160 rpm at 30° C. for 72 h. As the preculture, 10 ml of the medium having the same composition as above was placed in a test tube, sterilized with a speed autoclave, and inoculated with a loopful of said microorganism from a slant (ISP-2 agar medium (0.4% yeast extract (Oriental Yeast), 1.0% malt extract (Difco), 0.4% glucose (Sanei Toka), and 2% agar, at pH 7.3), and cultured with shaking at 30° C. for 72 h.

After the incubation, the culture medium was centrifuged at 8000 rpm (7000×g) for 20 min (a Hitachi Koki centrifuge himac SCR 20B with a RPR20-2-1451 rotor) to collect the microbial cells. The cells were washed with 50 mM Tris-HCl buffer (pH 7.5), centrifuged again at 8000 rpm (7000×g) for 20 min using the same rotor to obtain the cells to be used for the following processes. The cells were stored at −20° C.

(2) D-aminoacylase Activity Assay

The microbial cells obtained by the above-described method were ultrasonicated in 50 mM Tris-HCl (pH 7.5) at 200 W for 20 min using a sonicator (Kubota, Insonator 201M), and, then, centrifuged at 14000 rpm (20000×g) for 20 min with a Hitachi refrigerated centrifuge (using a RPR20-2-1451 rotor). The resulting supernatant was used as the crude D-aminoacylase solution.

The enzymatic reaction was carried out in a total volume of 1.0 ml of a reaction system containing 20 mM N-acetyl-D-methionine (Sigma), 50 mM Tris-HCl buffer (pH 7.5), 1 mM CoCl₂, and 100 μl of the enzyme solution at 30° C. for 60 min. The reaction was terminated by adding 0.5 ml of a TCA reaction terminating solution according to Tsai et al. (containing 0.11M trichloroacetic acid, 0.22M sodium acetate, and 0.33M acetic acid).

The enzyme activity was assayed according to TNBS method [Tokuyama, S., Hatano, K. and Takahashi, T., Biosci. Biotech. Biochem. 58, pp24 (1994)]. That is, a sample solution containing amino acid was added to 0.5 ml of the solution (C) (0.1M Na₂B₄O₇), and brought up to a volume of 1.0 ml. To this mixture was added 20 ml of 0.11M TNBS solution, and the resulting mixture was quickly mixed. Five min thereafter, absorption at 420 nm was measured.

In this assay, D-methionine was calorimetrically quantified with L-methionine as the standard, and one unit of enzyme was defined as the amount of enzyme to produce 1 μmol of D-methionine at 30° C. in 1 min.

Protein was quantified according to Lowry's method using bovine serum albumin (BSA) (Sigma) as the standard. That is, prior to the measurement, the solutions (A) [2% Na₂CO₃ (in 0.1N NaOH)] and (B) [0.5% CuSO₄ · 5H₂O (in 1% sodium citrate)] were mixed in a ratio of 50:1 to prepare an alkaline copper solution. One ml of the above alkaline copper solution was added to a protein sample (containing protein 5 to 50 μg) and the mixture was kept at room temperature for 20 min. Then, to the above reaction mixture was added a phenol reagent (acidity 1N) which had been diluted 2-fold with distilled water (0.1 ml), and the mixture was kept at room temperature for 30 min to effect the reaction. Then, its absorbance at 750 nm was measured.

By the above-described method, *Amycolatopsis orientaris* IFO 12806 was evaluated for its productivity of D-aminoacylase. As a result, this strain was found to have a relatively high activity of D-aminoacylase.

EXAMPLE 2

Purification of D-aminoacylase Derived from *Amycolatopsis orientalis* IFO 12806

1. Induction of D-aminoacylase

This microbial strain was cultured in ISP-2 liquid medium as used in Example 1 supplemented with or without N-acetyl-DL-methionine or DL-valine (Kanto Kagaku) (0.1% each) as the enzyme inducer with shaking at 160 rpm at 30° C. for 72 h.

After the incubation, the culture was centrifuged at 8000 rpm (7000×g) for 20 min with a Hitachi Koki refrigerated centrifuge to collect microbial cells. The cells were washed with 50 mM Tris-HCl buffer (pH 7.5) and then centrifuged again with the same centrifuge to harvest the cells to be used in the following processes. The cells were stored at −20° C.

The stored cells were suspended in 20 ml of 50 mM Tris-HCl (pH 7.5), ultrasonicated at 190 W for 10 min, and centrifuged with a Hitachi Koki refrigerated centrifuge at 14,000 rpm (20,000×g) for 20 min. The supernatant thus obtained was used as the crude enzyme solution.

The enzymatic reaction was performed in a total volume of 1.0 ml of a reaction system containing 20 mM N-acetyl-D-methionine, 50 mM Tris-HCl buffer (pH 7.5), 1 mM CoCl₂, and 100 μl of the enzyme solution at 30° C. for 10 min. The reaction was terminated by adding a TCA reaction terminating solution. Results of the production of D-aminoacylase in this microbial strain in the presence of the inducer are shown in Table 1.

TABLE 1

| Inducer | Wet cells (g) | Protein (mg/ml) | Activity (U/ml) | Total activity (U) | Specific activity (mU/mg) |
|---|---|---|---|---|---|
| No addition | 4.7 | 11.5 | 0.9 | 0.0 | 0.0 |
| N-acetyl-DL-methionine | 2.6 | 12.0 | 1.6 | 5.1 | 36.0 |
| DL-valine | 4.0 | 18.9 | 3.9 | 36.0 | 144.0 |

The results showed that, in this strain, D-aminoacylase is not induced in the absence of the inducer, indicating that this enzyme is an inducible enzyme, and induced more strongly with DL-valine rather than N-acetyl-DL-methionine, the substrate thereof.

2. Culture Method

This strain was cultured in 1 liter of a liquid medium [containing 1.5% polypeptone (Nihon Seiyaku), 0.5% yeast extract (oriental Yeast), 0.5% NaCl, 0.25% $K_2HPO_4$, and 1% glucose (Sanei Toka)] supplemented with 0.1% DL-valine as the D-aminoacylase inducer which was placed in a 5-liter Erlenmeyer flask at 160 rpm at 30° C. for 72 h. In this case, as the preproculture, the strain was cultured in 20 ml of the liquid medium having the same composition placed in a test tube at 30° C. for 72 h with shaking, and, as the preculture, it was cultured in 200 ml of the medium having the same composition except for containing 3% glycerol in place of glucose placed in a 500-ml Erlenmeyer flask at 160 rpm at 30° C. for 72 h.

After the incubation, the culture medium was centrifuged with a Hitachi Koki centrifuge (using a RPR10-2-443 rotor) at 10,000 rpm (17,000×g) for 20 min to harvest microbial cells. The cell pellet was washed with 50 mM Tris-HCl buffer (pH 7.5) and centrifuged again with the same centrifuge (using a RPRS4 373 rotor) at 4,000 rpm (3,500×g) for 30 min to harvest microbial cells, which were stored at −20° C.

3. Purification of D-aminoacylase (1) Examination of the Condition of Salting-out with Ammonium Sulfate In order to determine the condition for carrying out hydrophobic chromatography, the condition for the salting-out with ammonium sulfate was examined. A portion of microbial cells cultured by the above-described method was ultrasonicated (200 W, 30 min), and centrifuged with a Hitachi Koki centrifuge (using a RPR20-2-1451 rotor) at 15,000 rpm (30,000×g) for 20 min to prepare the crude enzyme solution. An aliquot of 10 ml each of this crude enzyme solution was brought to 10% to 40% saturation with ammonium sulfate (Wako Pure Chemicals Industries) respectively, stirred in ice-cold water for 1 h, and then centrifuged with a Hitachi Koki refrigerated centrifuge (using a RPR20-2-1451 rotor) at 15,000 rpm (30,000×g) for 20 min. The supernatant thus deprived of salted-out materials was dialyzed against a fully sufficient amount of 50 mM Tris-HCl buffer (pH 7.5) to remove ammonium sulfate, and then assayed for the enzyme activity.

(2) Bacteriolysis with Lysozyme

Ninety g of the microbial cells cultured and stored at −20° C. were suspended in 270 ml of 50 mM Tris-HCl buffer (pH 7.5). To this suspension was added 0.4 g of egg white lysozyme (Seikagaku Corporation), and the mixture was stirred at 30° C. for about 120 min to exude the enzyme. Since bacteriolysis with lysozyme resulted in the elution of DNA together with enzyme from microbial cells, making the suspension become viscous, 1 mg of DNase I (Sigma) was added thereto to degraded DNA. After lysis, the suspension was centrifuged with a Hitachi Koki refrigerated centrifuge (using a RPR20-2-1451 rotor) at 16,000 rpm (35,000×g) for 30 min to precipitate cell debris and obtain the supernatant (273 ml).

(3) Salting-out With Ammonium Sulfate

To the above-described supernatant was added cold and previously-pulverized-in-mortar ammonium sulfate in small portions until the solution reached 20% saturation. The mixture was stirred at 4° C. overnight. Salted-out materials were precipitated with a Hitachi Koki refrigerated centrifuge (using a RPR20-2-1451 rotor) at 15,000 rpm (3,000×g) for 20 min to obtain the supernatant (278 ml). As a result, this enzyme was not salted out with 20% saturated ammonium sulfate but salted out with 30% saturated ammonium sulfate (Table 2). Therefore, the supernatant was subjected to Butyl-Toyopearl column chromatography equilibrated with Tris-HCl buffer containing 20% saturated ammonium sulfate.

TABLE 2

|  | Total activity (U) | Specific activity (mU/mg) |
|---|---|---|
| cell-free extract | 594 | 67 |
| 10% fraction | 324 | 50 |
| 20% fraction | 474 | 90 |
| 30% fraction | 0 | 0 |
| 40% fraction | 0 | 0 |

(4) Butyl-Toyopearl Column Chromatography

The above-described supernatant (278 ml) was applied to a column (3.0×20 cm) of TSK-Gel Butyl-Toyopearl 650M (Tosoh) equilibrated with 50 mM Tris-HCl buffer (ph 7.5), to which 20% saturated ammonium sulfate had been added, for adsorption. After the column was washed with five column volumes of the same buffer, it was eluted by a linear gradient of 20%–0% saturated ammonium sulfate in five column volumes of the same buffer. Protein in each fraction was determined by measuring absorbance at 280 nm (FIG. 1).

(5) TLC Analysis

Figure 2:
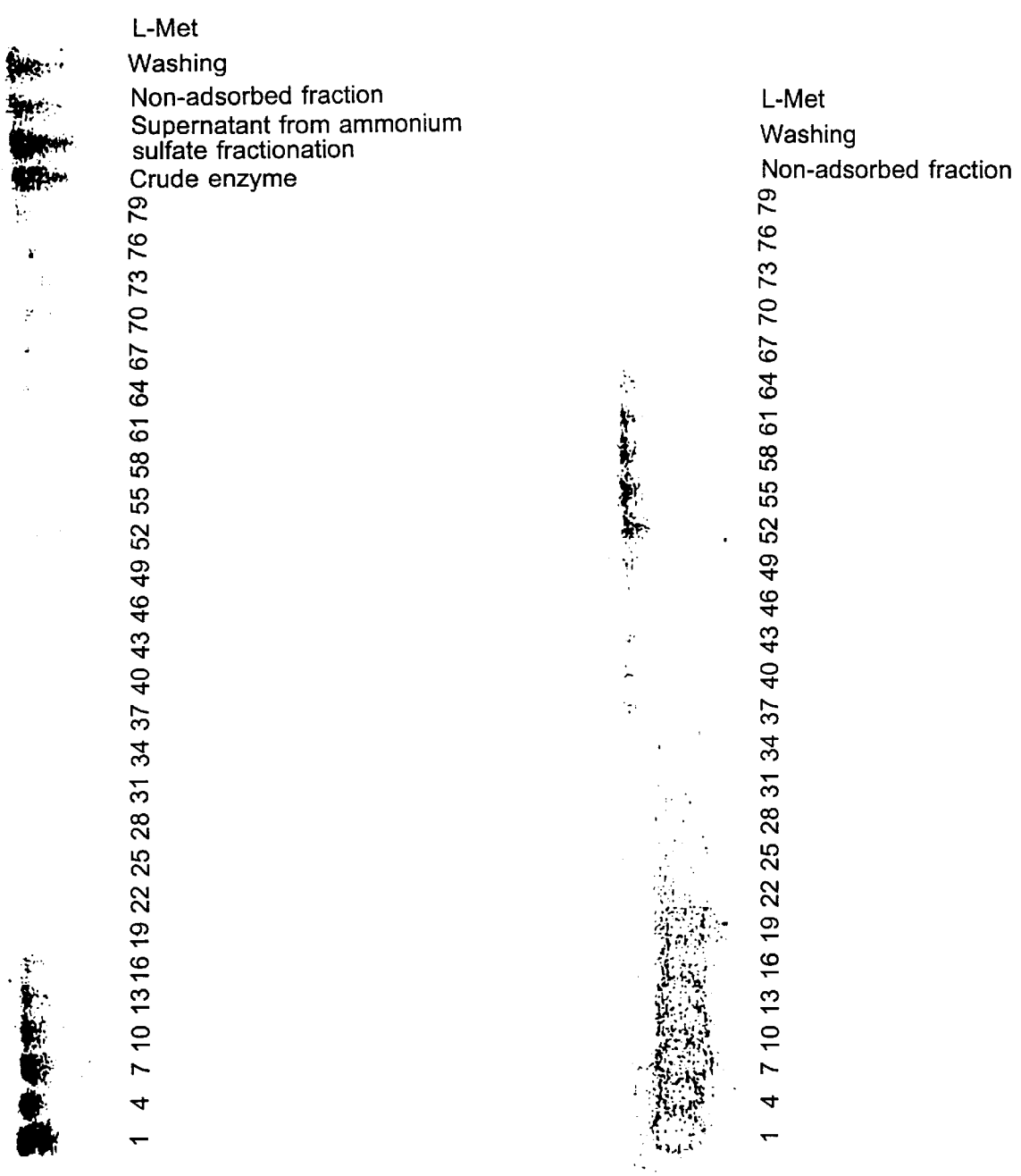
FIG. 2 shows the results of detection of activities of D-aminoacylase and L-aminoacylase by TLC method.

D-Aminoacylase activity in each fraction was measured in 50 mM Tris-HCl buffer (pH 7.5) containing 20 mM N-acetyl-D-methionine (a total volume of 500 µl) at 30° C. for 1 h. D-Methionine liberated was assayed by spotting an aliquot (about 3 µl) of each fraction on the TLC plate (Silica gel 60 F254, Merck) and developing it with a developing solvent of n-butanol:acetic acid:distilled water (3:1:1, by volume) using L-methionine as the standard, spraying the plate with a ninhydrin reagent (containing 0.2 g of ninhydrin, 95 ml of n-butanol, and 5 ml of 2N acetic acid), and heating the plate at about 170° C. to develop the color. In addition, in order to remove the L-aminoacylase activity, each fraction was similarly assayed by TLC for the D-aminoacylase activity using 20 mM N-acetyl-L-methionine as the substrate (FIG. 2). As a result, the L-aminoacylase activity was not found in non-absorbed fractions and washing fractions, but detected only in eluted fractions.

(6) DEAE-Toyopearl Column Chromatography

Active fractions obtained in the above-described Butyl-Toyopearl column chromatography were dialyzed against a sufficient volume of 50 mM Tris-HCl buffer (pH 7.5) to remove ammonium sulfate completely, thereby obtaining a crude enzyme solution (105 ml). This crude enzyme solution was applied to a column (3.0×16 cm) of TSK-Gel DEAE-Toyopearl 650M (Tosoh) (100 ml) which had been equilibrated with 50 mM Tris-HCl buffer (pH 7.5). The column was washed with five column volumes of the same buffer, and eluted with a linear gradient of 0–0.7M NaCl in five column volumes of the same buffer.

Figure 3:
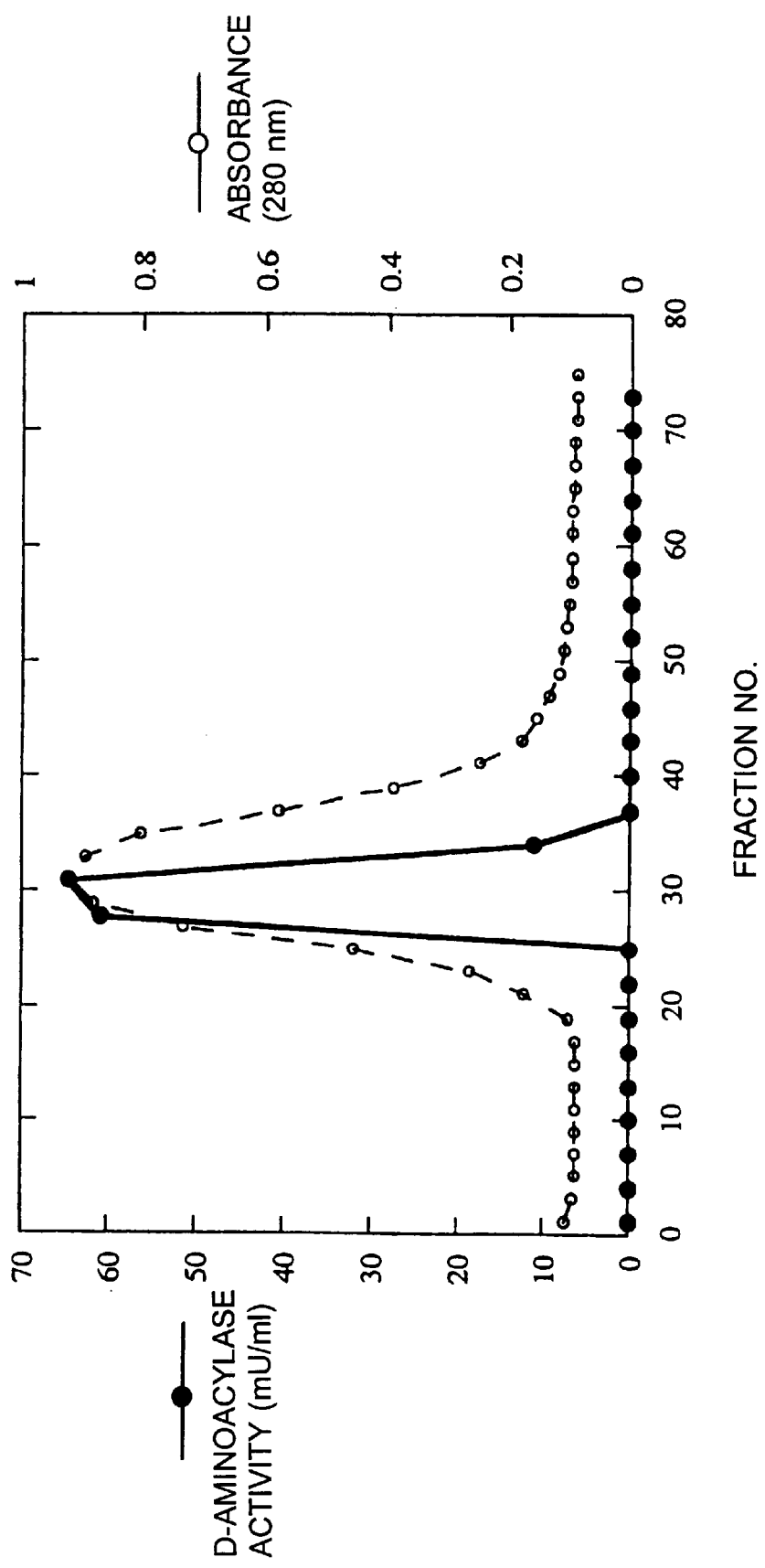
FIG. 3 shows the purification of D-aminoacylase of the present invention by DEAE-Toyopearl column chromatography.

D-Aminoacylase activity in each fraction was assayed in 50 mM Tris-HCl buffer (pH 7.5) containing 20 mM N-acetyl-D-methionine (a total volume of 1.0 ml) at 30° C. for 1 h. D-Methionine liberated was quantified calorimetrically by TNBS method using L-methionine as the standard. Results are shown in FIG. 3.

(7) Gel Filtration with Superose 12 HR 10/30

Figure 4:
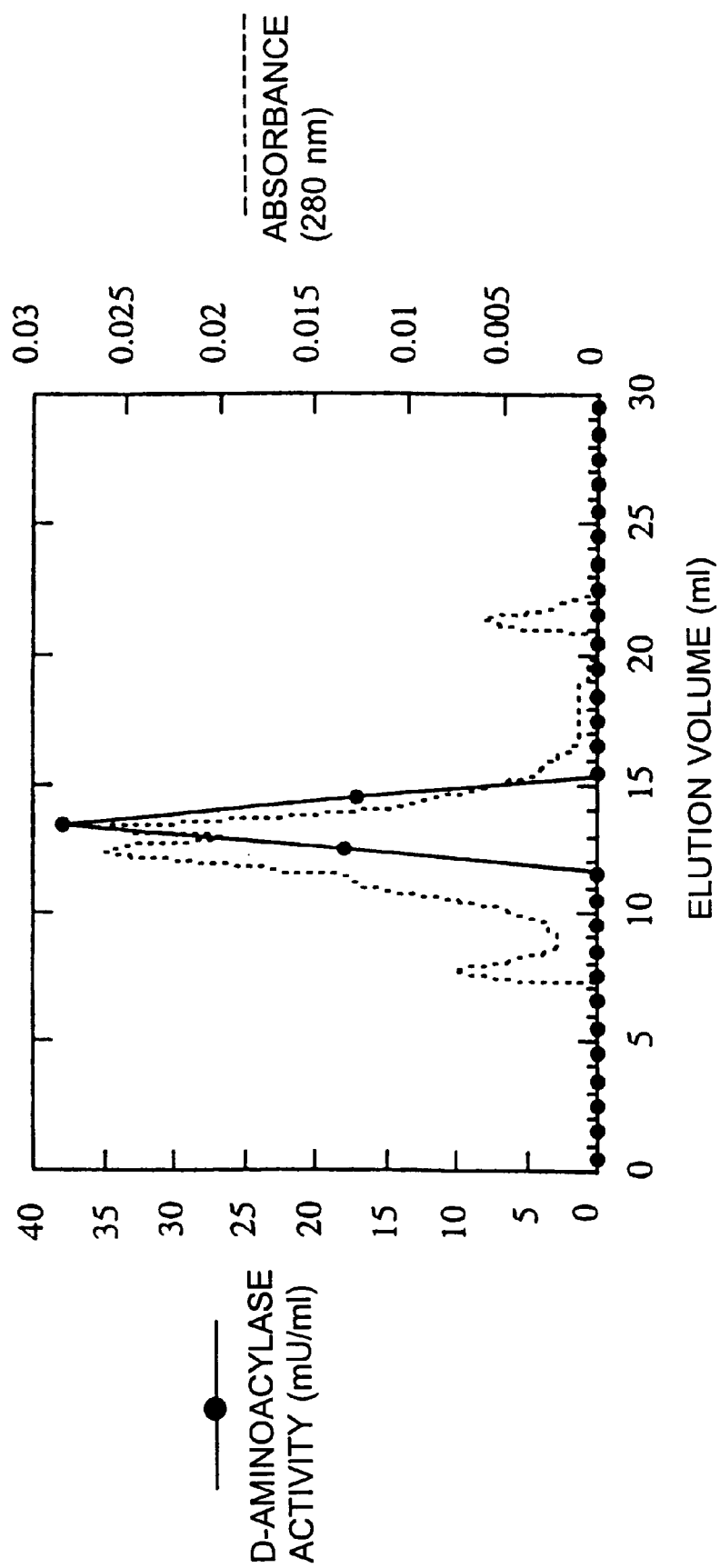
FIG. 4 shows the purification of D-aminoacylase of the present invention by gel filtration using Superose 12 HR 10/30.

Active fractions (fraction No.26–No.33) obtained in the above-described DEAE-Toyopearl column chromatography were combined (8 ml) and concentrated to 1 ml using a ultrafiltration membrane (Centricon, molecular weight cut-off: 10,000 (Grace Japan, Amicon)). This concentrated enzyme solution was applied to a column of Superose 12 HR 10/30 (Pharmacia) equilibrated with 50 mM Tris-HCl buffer (pH 7.5) containing 0.15M NaCl. The column was eluted with 30 ml of the same buffer at a flow rate of 0.4 ml/min, and fractionated in 1 ml portions (FIG. 4). As a result, the peak of D-aminoacylase activity was found at about 13 ml. The active fraction was subjected to SDS-polyacrylamide gel electrophoresis (SDS-PAGE).

(8) SDS-PAGE Method

According to the method of Laemmli (Laemmli, U.K., Nature 227, pp680), SDS-PAGE was performed at the constant current 30 mA using a Mini-PROTEAN II electrophoresis apparatus (Bio-Rad). While 4% polyacrylamide gel [in 0.125M Tris-HCl buffer (pH 6.8) containing 0.1% SDS] was used as stacking gel and 12% polyacrylamide gel [in 0.375M Tris-HCl buffer (pH 8.8) containing 0.1% SDS] was used as separation gel. The enzyme solution was mixed with an equal volume of the sample treatment solution (containing 0.0625M Tris-HCl (pH 6.8), 2% SDS, 20% glycerol, and 1% 2-mercaptoethanol) and maintained in a boiling water bath for about 2 min. After cooled to the room temperature, 20 μl of 0.5% bromophenol blue was added to this mixture, and an about 20 μl portion thereof was subjected to electrophoresis. As a result, a protein band seemingly to be D-aminoacylase of interest was observed.

EXAMPLE 3

Properties of D-aminoacylase Derived from *Amycolatopsis orientalis* IFO 12806

1. Determination of Molecular Weight

Molecular weight was determined by (1) gel filtration method and (2) SDS-polyacrylamide gel electrophoresis (SDS-PAGE) method.

(1) Gel Filtration Method

Figure 5:
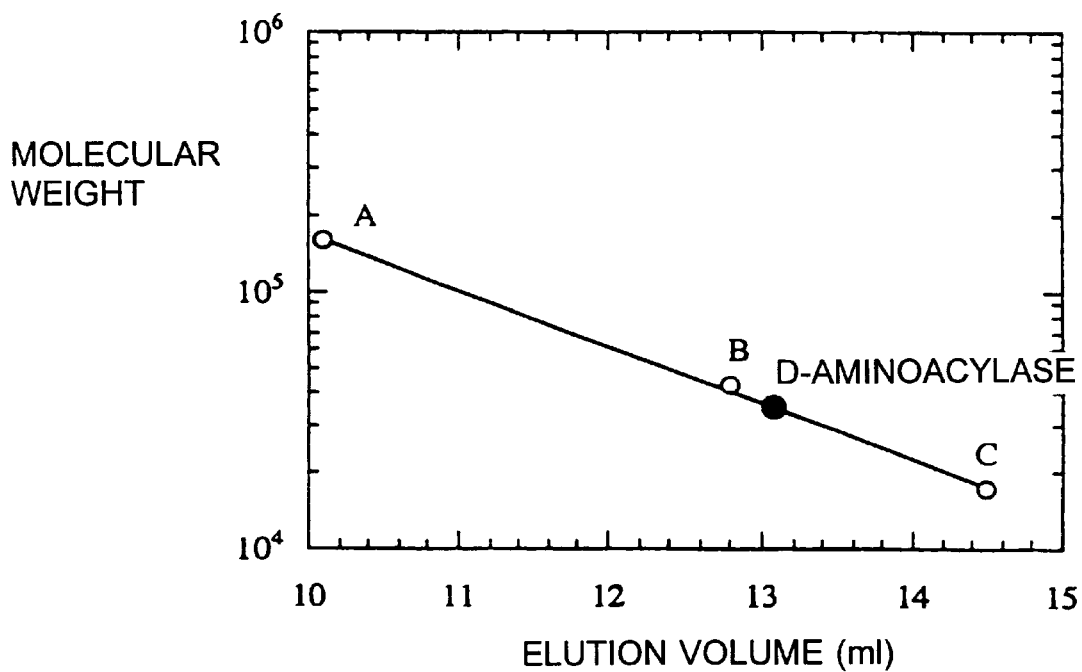
FIG. 5 shows the results of molecular weight determination of D-aminoacylase of the present invention by gel filtration. In the figure, A stands for gamma globulin (158 K), B for ovalbumin (44 K), and C for myoglobin (17 K).

The above-described Superose 12 HR 10/30 (Pharmacia) column was used. As the molecular weight standards, thyroglobulin (670 K), gamma globulin (158 K), ovalbumin (44 K), myoglobin (17 K), and vitamin B-12 (1.35 K). The flow rate was 0.4 ml/min. As a result, the molecular weight of the enzyme was estimated to be about 36,000 (FIG. 5).

(2) SDS-PAGE Method

Figure 6:
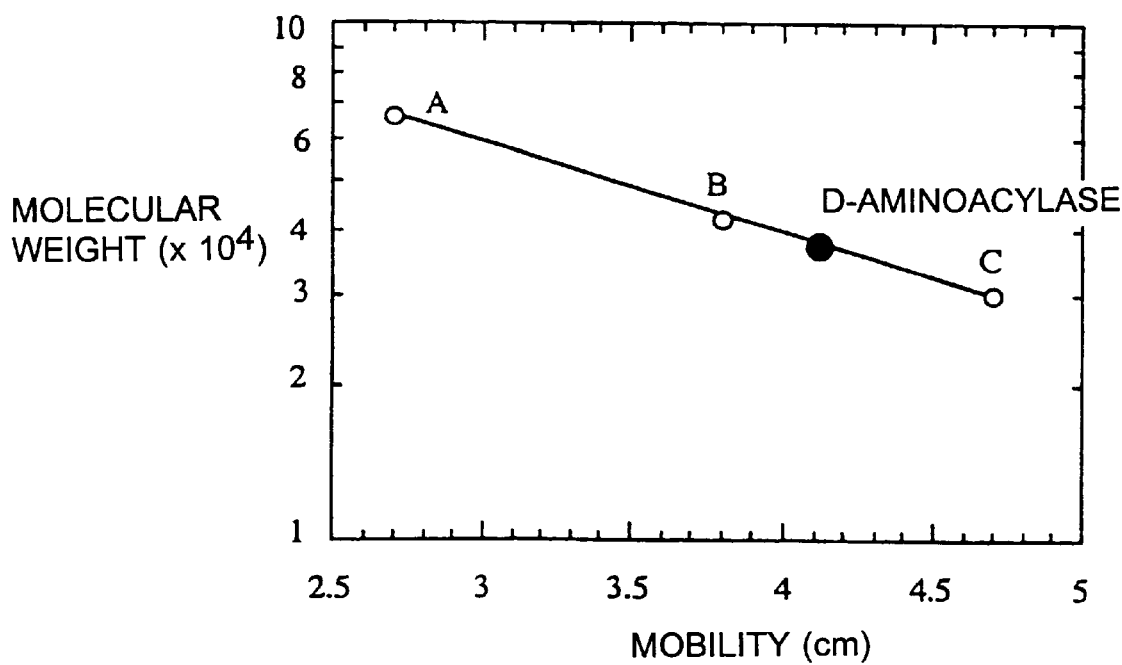
FIG. 6 shows the results of molecular weight determination of D-aminoacylase of the present invention by SDS-PAGE. In the figure, A stands for albumin (66 k), B for aldolase (42 k), and C for carbonic anhydrase (30 K).

According to the above-described method, SDS-PAGE was performed at the constant current of 30 mA using a Mini-PROTEAN II electrophoretic apparatus (Bio-Rad). As the protein molecular weight standards, a Daiichi III (Daiichi Kagaku Yakuhin) was used, comprising phosphorylase b (97 K), bovine serum albumin (66 K), aldolase (42 K), carbonic anhydrase (30 K), trypsin inhibitor (20 K), and lysozyme (14.4 K). After electrophoresis, gels were stained with Coomassie brilliant blue, successively treated with the decolorizing liquid I (containing 100 ml of acetic acid, 300 ml of methanol, and 700 ml of pure water) and the decolorizing liquid II (75 ml of acetic acid, 50 mlof methanol, and 875 ml of pure water), and then stained proteins were compared with molecular weight markers. As a result, the molecular weight of this protein was assumed to be about 36,000 (FIG. 6). Accordingly, it was assumed that D-aminoacylase derived from *Amycolatopsis orientalis* IFO 12806 is a monomer with the molecular weight about 36,000. Molecular weight of the present enzyme is smaller than that of D-aminoacylase from genus Alcaligenes (MI-4 strain, 51,000: A-6 strain, 52,000: DA1 strain 55,000, and DA181 strain 58,000), and also different from that of D-aminoacylase from genus Streptomyces (*S. olivaceus*, 45,000), being the smallest among D-aminoacylases hitherto reported.

2. Substrate Specificity

Substrate specificity of this enzyme was compared to, taking substrate specificity for N-acetyl-D-methionine as 100%, N-acetyl-D-valine, N-acetyl-D-phenylalanine, N-acetyl-D-leucine, N-acetyl-D-tryptophan, N-acetyl-D-asparagine, N-acetyl-L-methionine, N-acetyl-D-leucine, and N-acetyl-L-valine. The enzyme activity was assayed in 50 mM Tris-HCl buffer (pH 7.5) containing 100 μl of the enzyme solution and 20 mM of each substrate (total volume of 1.0 ml) at 30° C. for 3 h. Substrate specificity of this enzyme for N-acetyl derivatives of D-methionine, D-leucine, D-alanine, D-valine, D-tryptophan, D-asparagine, and D-phenylalanine is shown in Table 3.

TABLE 3

| Substrate | Specific activity (%) |
| --- | --- |
| N-acetyl-D-methionine | 100 |
| N-acetyl-D-leucine | 78 |
| N-acetyl-D-valine | 33 |
| N-acetyl-D-tryptophan | 54 |
| N-acetyl-D-asparagine | 19 |
| N-acetyl-D-phenylalanine | 36 |
| N-acetyl-D-alanine | 16 |
| N-acetyl-L-methionine | 0 |
| N-acetyl-L-leucine | 0 |
| N-acetyl-L-valine | 0 |

This enzyme acted well on N-acetyl-D-methionine and N-acetyl-D-leucine and acted somewhat on N-acetyl-D-phenylalanine, N-acetyl-D-tryptophan, N-acetyl-D-alanine, and N-acetyl-D-asparagine, whereas it did not act on N-acetyl-L-methionine, N-acetyl-L-leucine, and N-acetyl-L-valine.

Figure 7:
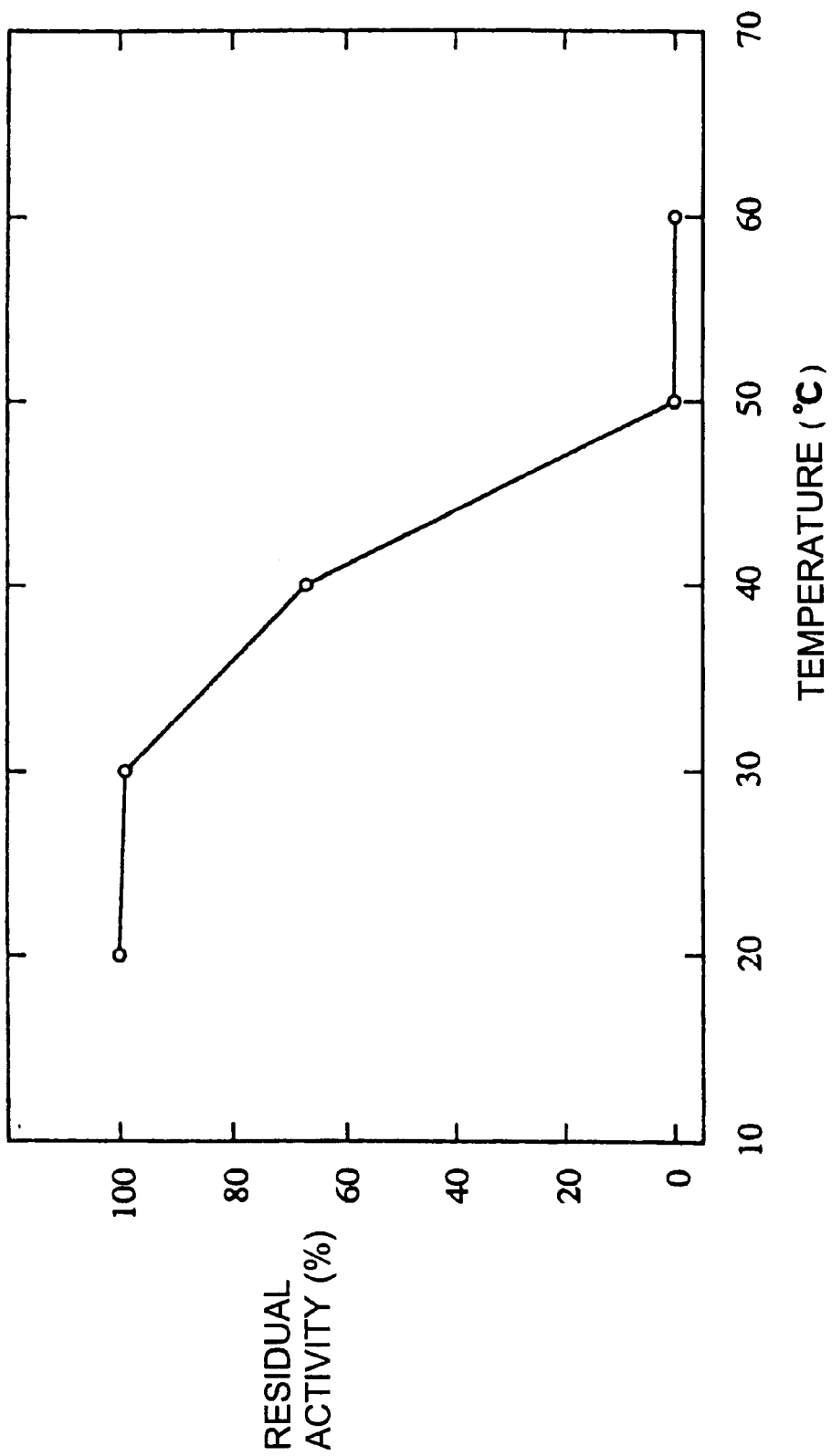
FIG. 7 shows the thermostability of D-aminoacylase of the present invention.

3. Property of the Enzyme (1) Thermostability of the Enzyme The enzyme solution was heated at 20° C., 30° C., 40° C. , 50° C., and 60° C. respectively, immediately cooled in ice, and the enzyme activity was assayed in 50 mM This-HCl buffer (pH 7.5) (total volume of 1.0 ml) at 30° C. for 30 min. Thermostability of this enzyme is shown in FIG. 7, indicating that the enzyme was relatively stable up to 40° C. , but inactivated at 50° C. or higher.

(2) Optimal Temperature for Reaction

Figure 8:
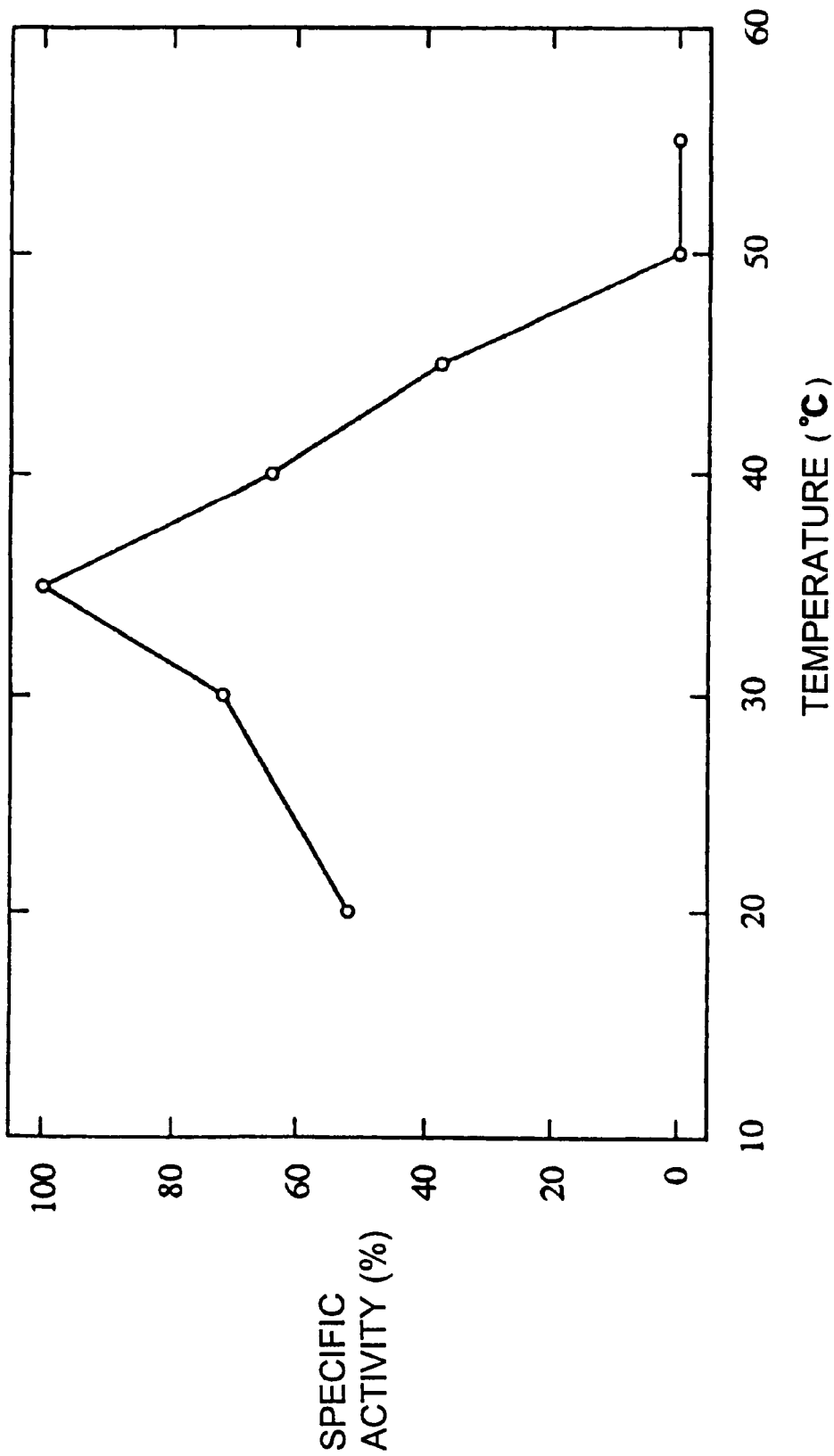
FIG. 8 shows the optimal reaction temperature of D-aminoacylase of the present invention.

Enzyme assay was performed in 50 mM This-HCl buffer (pH 7.5) (total volume of 1.0 ml) for 30 min varying only the temperature of the enzymatic reaction system from 20° C. to 50° C. The optimal temperature for the enzymatic reaction is shown in FIG. 8. From the results shown in FIG. 8, the optimal temperature of this enzyme was presumably about 35° C.

(3) Optimal pH for Reaction

Figure 9:
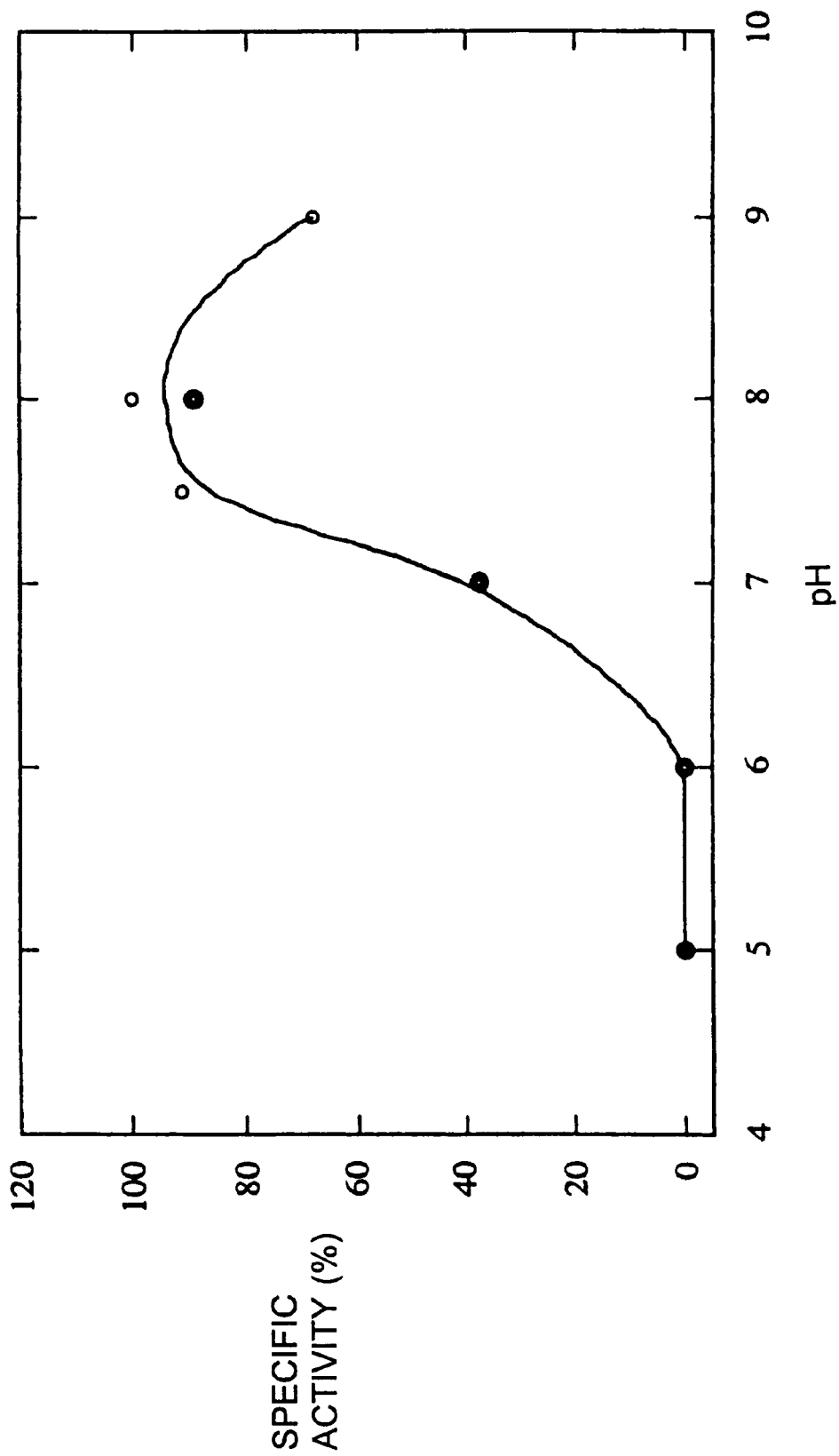
FIG. 9 shows the optimal reaction pH of D-aminoacylase of the present invention. In this figure, ● stands for $K_2HPO_4/NaH_2PO_4$ buffer, and ○ for Tris/HCl buffer.

Enzyme assay was performed in 50 mM This-HCl buffer (pH 7.5) (total volume of 1.0 ml) at 30° C. for 30 min varying only the pH of the enzyme reaction system from pH 5.0 to pH 9.0. As the buffers with pH 5.0, 6.0, 7.0, and 8.0, 50 mM $K_2HPO_4/NaH_2PO_4$ was used, while 50 mM Tris-HCl buffer was used as the buffers with pH 7.5, 8.0, and 9.0. The optimal pH of this enzyme is shown in FIG. 9. From the results shown in FIG. 9, the optimal pH of this enzyme was presumably about pH 8.0, and no activity was detected under the acidic conditions in the range from pH 5 to pH 6.

(4) Influences of Various Metallic Salts and Reagents

Enzyme assay was performed in 50 mM Tris-HCl buffer (pH 7.5) (total volume of 500 μl) at 30° C. for 60 min with the addition of various metallic salts and enzyme inhibitors to the enzymatic reaction system to give the concentration of 1 mM or 10 mM. Influences of various metallic salts and reagents on the activity of this enzyme are shown in Tables 4 and 5. In Table 5, the term "PCMB" means p-chloromercuribenzoic acid.

TABLE 4

| Metallic ions | Methionine produced (mM) Concentration 1 mM | Methionine produced (mM) Concentration 10 mM | Specific activity (%) Concentration 1 mM | Specific activity (%) Concentration 10 mM |
|---|---|---|---|---|
| No addition | 0.25 | 0.25 | 100 | 100 |
| $Mg^{2+}$ ($MgCl_2$) | 0.32 | 0.32 | 128 | 92 |
| $Mn^{2+}$ ($MnCl_2$) | 0.24 | 0 | 96 | 0 |
| $Fe^{2+}$ ($FeCl_2$) | 0.13 | 0 | 52 | 0 |
| $Co^{2+}$ ($CoCl_2$) | 0.52 | 0.27 | 208 | 108 |
| $Zn^{2+}$ ($ZnCl_2$) | 0 | 0 | 0 | 0 |
| $Ni^{2+}$ ($NiCl_2$) | 0.12 | 0.17 | 48 | 68 |
| $Ca^{2+}$ ($CaCl_2$) | 0.45 | 0.52 | 180 | 208 |
| $Ba^{2+}$ ($BaCl_2$) | 0.19 | 0.44 | 86 | 176 |
| $Hg^{2+}$ ($HgCl_2$) | 0 | 0 | 0 | 0 |
| $Cu^{2+}$ ($CuCl_2$) | 0 | 0 | 0 | 0 |
| $K^+$ (KCl) | 0.13 | 0.21 | 52 | 84 |
| $Na^+$ (NaCl) | 0.21 | 0.36 | 84 | 152 |

TABLE 5

| Reagents | Methionine produced (mM) Concentration 1 mM | Methionine produced (mM) Concentration 10 mM | Specific activity (%) Concentration 1 mM | Specific activity (%) Concentration 10 mM |
|---|---|---|---|---|
| No addition | 0.22 | 0.22 | 100 | 100 |
| PCMB | 0 | 0 | 0 | 0 |
| iodoactate | 0.14 | 0.11 | 64 | 50 |
| dothiothreitol | 0.17 | 0.15 | 77 | 68 |
| N-ethyl-maleimide | 0.1 | 0 | 45 | 0 |
| EDTA.2Na | 0 | 0 | 0 | 0 |

Activity of this enzyme was significantly promoted by divalent cations such as 1 mM $Co^{2+}$ and $Ca^{2+}$, while inhibited by $Cu^{2+}$ and $Hg^{2+}$. $Co^{2+}$ activated the enzyme at 1 mM, but did not do so at 10 mM. On the other hand, $Ca^{2+}$ did not inhibit the enzyme activity even at 10 mM. This enzyme was inhibited by SH-reagent such as PCMB (p-chloromercuribenzoic acid) and iodoacetate, and also by the metal chelating agent EDTA.

What is claimed is:

1. A purified D-aminoacylase having the following physicochemical properties that:
   (a) action: it acts on N-acetyl-D-amino acids to produce corresponding D-amino acids;
   (b) molecular weight: it has the molecular weight of about 36,000 dalton when measured by SDS-polyacrylamide gel electrophoresis;
   (c) substrate specificity: it acts on N-acetyl-D-methionine, N-acetyl-D-valine, N-acetyl-D-tryptophan, N-acetyl-D-asparagine, N-acetyl-D-phenylalanine, N-acetyl-D-alanine, and N-acetyl-D-leucine, but not on N-acetyl-L-methionine, N-acetyl-L-leucine, and N-acetyl-L-valine;
   (d) thermostability: when heated at pH 7.5 for 30 min, it is relatively stable at 40° C., but inactivated at not less than 50° C.;
   (e) optimal temperature: when reacted at pH 7.5, it optimally acts at about 35° C.;
   (f) optimal pH: when reacted at 30° C. for 60 min, it optimally acts at about pH 8.0; and
   (g) influences of metallic ions: its enzyme activity is promoted by 1 mM $Co^{2+}$ or $Ca^{2+}$, but inhibited by 1 mM $Cu^{2+}$, $Hg^{2+}$, or $Zn^{2+}$.

2. The D-aminoacylase according to claim 1, wherein said enzyme is derived from a microorganism belonging to genus Amycolatopsis.

3. The D-aminoacylase according to claim 1, wherein said enzyme is derived from *Amycolatopsis orientalis*.

4. A method for producing D-aminoacylase, which comprises culturing a microorganism belonging to genus Amycolatopsis and recovering from the cultured microbial cells an enzyme having the following physicochemical properties:
   (a) action: it acts on N-acetyl-D-amino acids to produce corresponding D-amino acids;
   (b) molecular weight: it has the molecular weight of about 36,000 dalton when measured by SDS-polyacrylamide gel electrophoresis;
   (c) substrate specificity: it acts on N-acetyl-D-methionine, N-acetyl-D-valine, N-acetyl-D-tryptophan, N-acetyl-D-asparagine, N-acetyl-D-phenylalanine, N-acetyl-D-alanine, and N-acetyl-D-leucine, but not on N-acetyl-L-methionine, N-acetyl-L-leucine, and N-acetyl-L-valine;
   (d) thermostability: when heated at pH 7.5 for 30 min, it is relatively stable at 40° C., but inactivated at not less than 50° C.;
   (e) optimal temperature: when reacted at pH 7.5, it optimally acts at about 35° C.;
   (f) optimal pH: when reacted at 30° C. for 60 min, it optimally acts at about pH 8.0; and
   (g) influences of metallic ions: its enzyme activity is promoted by 1 mM $Co^{2+}$ or $Ca^{2+}$, but inhibited by 1 mM $Cu^{2+}$, $Hg^{2+}$, or $Zn^{2+}$.

5. The method for producing D-aminoacylase according to claim 4, wherein said microorganism belonging to genus Amycolatopsis is *Amycolatopsis orientalis*.

6. The method for producing D-aminoacylase according to claim 4, wherein said microorganism is cultured in the presence of an inducer.

7. A method for producing D-amino acid, which comprises reacting the D-aminoacylase according to claim 1 with N-acetyl-DL-amino acid and recovering D-amino acid from the reaction system.

8. The method for producing D-amino acid according to claim 7, wherein said N-acetyl-DL-amino acid is selected from the group consisting of N-acetyl-DL-methionine, N-acetyl-DL-valine, N-acetyl-DL-tryptophan, N-acetyl-DL-asparagine, N-acetyl-DL-phenylalanine, N-acetyl-DL-alanine, and N-acetyl-DL-leucine.

* * * * *